United States Patent [19]

Cordle et al.

[11] Patent Number: 5,260,057
[45] Date of Patent: Nov. 9, 1993

[54] METHOD AND PRODUCT FOR THE TREATMENT OF GASTRIC DISEASE

[75] Inventors: Christopher T. Cordle, Centerburg; Joseph P. Schaller, Columbus, both of Ohio

[73] Assignee: Abbott Laboratories, Abbott Park, Ill.

[21] Appl. No.: 999,233

[22] Filed: Dec. 31, 1992

Related U.S. Application Data

[60] Division of Ser. No. 926,181, Aug. 7, 1992, which is a continuation of Ser. No. 559,793, Jul. 30, 1990, abandoned.

[51] Int. Cl.$^5$ ............... A61K 39/395; C07K 15/28; C07K 15/00
[52] U.S. Cl. ............... 424/85.8; 424/87; 530/388.4; 530/387.1; 530/389.1
[58] Field of Search ............... 424/85.8, 87; 530/388.4, 387.1, 389.1

[56] References Cited

U.S. PATENT DOCUMENTS

| | | | |
|---|---|---|---|
| 3,128,230 | 4/1964 | Heinbach | 424/86 |
| 3,984,539 | 10/1976 | Khuow et al. | 424/87 |
| 3,992,521 | 11/1976 | LeMinor | 424/87 |
| 4,051,235 | 9/1977 | Plymate | 424/85.8 |
| 5,143,727 | 9/1992 | Ebina | 424/89 |

FOREIGN PATENT DOCUMENTS 1573995  9/1980  United Kingdom.

OTHER PUBLICATIONS

"Bovine Milk Immunoglobulins (Ig), Their Possible Utilization in Industrially Prepared Infant's Milk Formulae", Hilpert et al, *XII Symposium of the Swedish Nutritional Foundation*, pp. 182–196 (1977).

"Treatment of Infantile *E. coli* Gastroenteritis with Specific Bovine Anti *E. coli* Milk Immunoglobulins", Mietens et al., *European Journal of Pediatrics*, 132:239–252 (1979).

"Prevention of Rotavirus Infection by Cow Colostrum Containing antibody Against Human Rotavirus", Ebina et al, *The Lancet*, pp. 1029–1030, Oct. 29, 1983.

*Laboratory Techniques in Biochemistry and Molecular Biology, Monoclonal Antibody Technology*, edited by Burdon et al, pp. 1–32 (1984).

"Prevention of rotavirus infection by oral administration of cow colostrum containing anti human rotavirus antibody", Ebina et al., *Medical Microbiology & Immunology*, 174:177–185 (1985).

"Monoclonal antibodies directed against the flagella of *Campylobacter jejuni*", Newell, *J. Hyg. Camb.*, 96:131–141 (1986).

"Protection against *Campylobacter jejuni* Infection in Suckling Mice by Anti-Flagellar Antibody", Ueki et al., *Microbiol. Immunol.*, 31:(12)1161–1171 (1987).

*Campylobacter pylori*, Raws & Tytgat editors, pp. 89–103 and 138–139 (1989).

*Primary Examiner*—Y. Christina Chan
*Assistant Examiner*—Susan A. Loring
*Attorney, Agent, or Firm*—Lonnie R. Drayer; Donald O. Nickey

[57] ABSTRACT

This invention describes a product obtained from the isolation and concentration of specific immunoglobulins (antibodies) derived from the mammary secretions of cows immunized with *Helicobacter pylori*. The product is useful in preparing formulations for the treatment and/or prevention of gastric diseases.

2 Claims, No Drawings

METHOD AND PRODUCT FOR THE TREATMENT OF GASTRIC DISEASE

This is a divisional of application Ser. No. 07/926,181 filed Aug. 7, 1991, now pending which is a continuation of application Ser. No. 07/559,793 filed on Jul. 30, 1990, now abandoned.

TECHNICAL FIELD

This invention relates to the isolation of specific immunoglobulins which, in the preferred embodiment, are isolated from the colostrum or milk of cows immunized with *Helicobacter pylori*. This invention is also directed to a method of use of these specific antibodies in the preparation of novel formulations useful in the enteral treatment of gastric disease.

BACKGROUND

The present invention relates to a process for the production of a protein concentrate containing immunological factors preferably of lactic origin and to a specific immunoglobulin population. More particularly, this invention relates to active immunoglobulins exhibiting specificity against the microorganism, *Helicobacter pylori* (formerly referred to in the literature as *Campylobacter pylori*) and the use of this protein in the management of *Helicobacter pylori* colonization in the gastrointestinal (GI) tract. More specifically, the present invention relates to the injection of lactating mammals with *Helicobacter pylori*, subsequent isolation and concentration of antibodies from the colostrum (or milk) produced by the immunized mammals and use of this concentrate, by way of enteral ingestion, in reducing the infectivity of *Helicobacter pylori* resident in the gastrointestinal tract. This protein (immunoglobulin) concentrate is useful in the treatment of pathological sequela associated with *Helicobacter pylori* colonization of the GI tract including gastritis and peptic ulcer disease.

In general, the prior art discloses the introduction and use of immunological factors of lactic origin into-dietetic products for newborn babies and infants. The oral ingestion of these dietetic products being intended to enable these immunological factors to be utilized in the development of protection against the consequences of microbial infection within the GI tract.

U.S. Pat. Nos. 3,992,521 and 3,984,539 disclose a process for obtaining an immune product containing antibodies from the serum of a horse or cow and the immunoglobulin product itself. These patents do not suggest nor disclose the specific immunoglobulin of the present invention, nor its method of production and isolation, nor its intended method of use for the treatment of *Helicobacter pylori* induced gastritis.

U.S. Pat. No. 3,128,230 discloses a method for producing antibodies which consists of injecting a lactating mammal with a mixture of killed microorganisms and isolating the antibodies from serum or milk. This patent does not suggest nor disclose that *Helicobacter pylori* can induce an antibody response nor the specific method of treatment employed in this invention.

British Patent No: 1,573,995 discloses and claims a process for the production and isolation of immunoglobulins exhibiting specificity against *Escherichia coli*. This patent does not suggest that microorganisms other than *E. coli* are useful. In similar fashion, the following references disclose the same type of process: 1) H. Hilpert, et al., Proceedings of the 13th Symposium Swedish Nutritional Foundation; and 2) C. Mietens, et al., European J. Pediatrics, 132, 239–252, (1979).

Ebina and colleagues disclose the immunization of cows with human rotavirus and the isolation of immunoglobulin to the virus from the milk of cows. This immunoglobulin was orally administered to children and was found to reduce the frequency of the outbreak of diarrhea. See Ebina, et al. The Lancet (Oct. 29, 1983), 1029–1030, (1983); and Ebina, et al., Med. Microbioi. Immunol., 174, 177–185, (1985). These references do not suggest nor disclose that immunoglobulins to *Helicobacter pylori* would be useful in the management *Helicobacter pylori* induced gastritis.

U.S. Pat. No. 4,051,231 discloses the isolation of immunoglobulins from the milk of vaccinated cows by coagulating the milk, recovering the lactoserum (whey) and selectively precipitating-the immunoglobulins with ammonium sulfate, followed by dialysis against water, filtration and drying. Seroprotection tests demonstrated that the protein concentrates of U.S. Pat. No. 4,051,231 provided local passive immunity in the intestine without resorption and without any significant loss of activity in the digestive tract, thereby providing generalized passive protection against certain enteropathogenic bacteria and/or viruses. This patent does not suggest nor disclose that such antibodies could serve to modify the course of *Helicobacter pylori* induced gastritis.

Much has been published regarding *Helicobacter pylori* itself. *Helicobacter pylori* is approximately 0.85 um in diameter with an average length of 2.9 um. The microorganism has a smooth coat and four to six polar flagella which are sheathed and have bulbous ends. In fresh cultures this organism appears as a slender, curved Gram-negative rod. *Helicobacter pylori* is readily distinguished from other gastric bacteria and spirochaetes by the absence of axial filaments in its flagella. Furthermore, optimum growth conditions for *Helicobacter pylori* are unusual and help to set it apart from other enteropathogens. For example, *Helicobacter pylori* requires a microaerophilic gas environment (i.e. low oxygen content) to sustain growth. *Helicobacter pylori* appears to tolerate a wide range of local pH conditions and is relatively resistant to acid conditions. It is believed that this resistance is due in part to the organism's outer protein structure which contains urease in large amounts resulting in the cleavage of urea naturally present in gastric fluid and hence, the formation of a buffering ammonia layer immediately around the organism.

Although a number of spiral bacteria inhabit the mouth and lower intestinal tract of all mammals, what distinguishes *Helicobacter pylori* is the observation that it is localized almost exclusively to the luminal mucosal surface of the stomach and duodenum and generally is found deep within the gastric pits.

It is the combination of the unusual growth requirements and intestinal location which makes eradication and treatment of *Helicobacter pylori* so difficult. The ideal antimicrobial drug suitable for the successful treatment of *Helicobacter pylori* associated gastritis should exhibit local activity, be stable at low pH values and should be able to readily penetrate the gastric mucosa. These desirable properties of an antimicrobial are not easily accomplished and thus, satisfactory treatment of *Helicobacter pylori* with antimicrobials has yet to be accomplished.

The development of an agent which is effective in the management of *Helicobacter pylori* induced gastritis would fulfill a long felt need. There is an emerging consensus in the field of gastroenterology that *Helicobacter pylori* is a major contributing-factor in the development of gastritis and septic ulcer disease. Specifically, the following reference is useful in establishing the background of the present invention: *Campylobacter pylori*, E. A. J. Rauns and G. N. J. Tytgat, Editors, Adis Press Intntl. (1989).

In general, this reference discloses, at pages 138-139, the role of *Helicobacter pylori* in the development of gastritis and peptic ulcer disease. The key evidence in support of *Helicobacter pylori* etiology in these conditions is based on the observation, at pages 89-103, that elimination of *Helicobacter pylori* from the stomach through the use of antibiotics and/or bismuth compounds leads to a remission of the gastric disease.

Presently, the main therapies employed in the treatment of chronic active gastritis and peptic ulcer disease include the histamine H2-receptor antagonists, bismuth compounds, and antibiotics. However, it is generally accepted that all currently used treatment modalitites are clinically inadequate since post-treatment relapse rates remain unacceptably high. In addition, several of these therapies are accompanied by significant side effects. For example, effective antibiotic treatment of *Helicobacter pylori* infections requires treatment over an extended duration (4-6 weeks) and results in the induction of diarrhea and intestinal discomfort. The bismuth compounds are also known to have a number of significant undesirable side effects.

To date, the preferred treatment has been dominated by the use of H2-antagonists which result in the suppression of acid and pepsin secretion; however, post treatment relapse rates are extremely high. Since symptomatic relief and ulcer healing are the primary aim of treatment, without indefinite maintenance therapy, it is becoming increasingly apparent that a mucosal "protective agent" having antimicrobial activity against *Helicobacter pylori*, is desirable.

Thus, the medical community has a need for a protective agent which can be readily utilized in pharmaceutical and/or nutritional formulations. The present invention fulfills that need through the discovery that enteral ingestion of immunoglobulins derived from lactating mammals immunized with *Helicobacter pylori* provides such protection.

The prior art fails to suggest, disclose or contemplate the instant discovery which is, in part, the use of antibodies (immunoglobulin) in the treatment of *Helicobacter pylori* infection of the gastric mucosa and to the antibodies themselves.

Lactile secretion derived antibodies obtained from cows immunized with *Helicobacter pylori* will provide numerous advantages over other methods of immunoglobulin production. The advantages include quantity, ease and reproducibility of immunoglobulin isolation, ease of product preparation and significant cost savings as compared to antibody and product preparation based on other isolation methods.

One aspect of the present invention relates to a method for producing a milk based product having high immunological specific activity against *Helicobacter pylori*.

Another further aspect of this invention is the specific immunoglobulin itself which is produced according to the disclosed method.

A further aspect of the present invention relates to a method for treating mammals in order to produce milk having immunological components which provide protection against *Helicobacter pylori* to subjects imbibing same.

A further aspect of this invention is the use of these specific antibodies (immunoglobulins) in the treatment of *Helicobacter pylori* induced gastritis.

DISCLOSURE OF THE INVENTION

There is disclosed a composition of matter consisting of non-denatured immunoglobulins which exhibit specific activity to the bacterium *Helicobacter pylori*. More specifically, an immunoglobulin isolated from the mammary secretions of mammals exhibiting specific activity towards *Helicobacter pylori*.

There is also disclosed a medicament for gastritis caused by *Helicobacter pylori* which comprises non-denatured immunoglobulin which exhibits specificity towards *Helicobacter pylori*. The disclosed medicament may be used alone or in combination with a pharmacologically and/or nutritionally acceptable carrier and may be in a powdered or liquid form.

There is further disclosed a method for treating an individual suffering from *Helicobacter pylori* induced gastritis, peptic ulcer disease or other diseases said method consisting of administration to the individual in need of treatment an effective amount of a composition which contains at least the non-denatured immunoglobulins having specificity against *Helicobacter pylori*.

There is also disclosed a method for producing immunoglobulins exhibiting specificity for *Helicobacter pylori* which comprises the steps of 1) immunizing a lactating or pregnant mammal with a cell suspension of *Helicobacter pylori* emulsified in an adjuvant; 2) obtaining the colostrum or milk from the mammal and 3) isolating the immunoglobulins from the secretion.

In general, the composition of matter of this invention is derived by a process which comprises the isolation of immunoglobulins from the mammary secretions of mammals immunized with *Helicobacter pylori*, said immunoglobulins exhibiting specific antimicrobial activity against *Helicobacter pylori*.

The method for the treatment of *Helicobacter pylori* infections, comprises the oral ingestion of an effective amount of *Helicobacter pylori*-specific immunoglobulins by a patient in need of treatment, said immunoglobulins being derived from the mammary secretions of mammals immunized with *Helicobacter pylori*. The immunoglobulins may be ingested alone or in combination with other materials such as fats, oils and proteins.

In its broadest aspect the present invention is directed to novel compositions which demonstrate antimicrobial activity against *Helicobacter pylori*.

The novel composition of matter of this invention consists of the immunoglobulins isolated from the mammary secretions of mammals immunized with *Helicobacter pylori* which may be utilized alone or combined with other natural or synthetic edible products such as lipids, proteins or oils. Said composition of matter is readily employed alone or in combination with other edible products to yield admixtures which are useful in the treatment of gastric diseases.

Other aspects and advantages of the invention will be apparent upon consideration of the following detailed description of the illustrative embodiments hereof.

BEST MODE

The utility of this invention was demonstrated by the ingestion of the specific antibody (immunoglobulins) of this invention by *Helicobacter pylori* infected germ free piglets. Ingestion of a nutritional containing the specific antibody (immunoglobulins) of this invention provided the reduction or elimination of *Helicobacter pylori* induced pathology as well as a reduction in *Helicobacter pylori* bacterium colonization levels in various gastric epithelium regions, as determined by both agar plate culture reisolation and by histologic methods.

Specific antibody to *Helicobacter pylori* was raised in cows (as described in detail below) and characterized by standard immunochemical techniques as described below. Additional characterization of the antibodies can be achieved, for example, through the assessment of their ability to agglutinate *Helicobacter pylori*, their ability to fix complement in the presence of the *Helicobacter pylori* bacteria, the ability of the antibodies to inhibit bacterial replication and their ability to specifically bind the *Helicobacter pylori* bacterial antigens as detected by common immunochemical methods such as immunofluorescence and the like.

Following immunochemical characterization, the *Helicobacter pylori* specific antibodies were fed to *Helicobacter pylori* monoinfected gnotobiotic piglets according to the feeding regimen described below. Following feeding of *Helicobacter pylori* specific antibody, blood samples were drawn and the animals sacrificed for subsequent microbiological and histopathological assessment of the treatment protocol. The results of these studies were compared to *Helicobacter pylori* monoinfected gnotobiotic piglet littermates fed a nonimmune milk based on the nutritional product Similac ® (infant nutritional product of Ross Laboratories, Division of Abbott Laboratories, Columbus, Ohio) which does not contain specific *Helicobacter pylori* antibodies.

As a result of these experiments, the inventors have discovered that enteral ingestion of an the immunoglobulin product containing specific antibodies to *Helicobacter pylori* results in the reduction in the levels of viable *Helicobacter pylori* contained within various regions of the stomach and as such provides a realistic approach for the treatment of *Helicobacter pylori* induced gastritis. The *Helicobacter pylori* specific antibodies may be employed alone (i.e. in a liquid, tablet or capsule form) or in combination with other pharmaceutically acceptable carriers such as various lipids, proteins or oils which may also provide additional nutritional and/or pharmaceutical benefits.

EXPERIMENTAL

The following examples relate to the production and use of specific antibodies to *Helicobacter pylori* and the physiological results of such usage. More specifically Examples 1 and 2 relate to the production and characterization of the immunoglobulin material isolated from pregnant cows immunized with *Helicobacter pylori* bacteria. Table 1 sets forth the immunological characterization of the colostrum whey products isolated from cows immunized with *Helicobacter pylori* as compared to non-immunized (i.e. control) cows. This data indicates that the concentration of *Helicobacter pylori* specific antibody (immunoglobulins) levels contained in whey provided by *Helicobacter pylori* immunized cows increased by over one hundred fold as compared to non-immunized cows. Example 3 relates to the biophysical and biological characterization of the specific immunoglobulins isolated from immunized versus non-immunized cows and exhibiting activity specifically against *Helicobacter pylori*. Tables 2 and 3 summarize the biological and biophysical data respectively.

Examples 4, 5 and 6 relate to the formulation and use of this immune material in the feeding of gnotobiotic pigs preinfected with *Helicobacter pylori* and thus, of the utility of this material in the treatment of *Helicobacter pylori* induced gastritis. The data contained in Table 4 indicates clearly that animals exposed to *Helicobacter pylori* through oral ingestion as described in Example 5 develop systemic (sera contained) antibodies to *Helicobacter pylori*, thereby confirming the effectiveness of oral treatment with *Helicobacter pylori* as a means of achieving *Helicobacter pylori* infection.

Example 7 relates to the assessment of the effect of feeding this immune material on the levels of viable *Helicobacter pylori* bacteria which can subsequently be recovered from various gastric epithelial sites of piglets preinfected with *Helicobacter pylori*. Tables 5 and 6 summarize these results. The data indicate markedly reduced recoveries of viable *Helicobacter pylori* from all gastric regions examined for animals fed the immune product as compared to animals which received the nonimmune nutrient only. These results clearly indicate the effectiveness of using *Helicobacter pylori* specific antibodies (immunoglobulins) in the treatment of *Helicobacter pylori* induced gastritis.

Best Mode For Carrying Out The Invention

EXAMPLE 1

Preparation of Antibodies and Control Products

Whey containing *Helicobacter pylori* specific antibodies was prepared from colostrum derived from a cow immunized while pregnant with whole formalin killed *Helicobacter pylori* bacteria (ATTCC Strain 26695). The bacteria, emulsified in incomplete Freund's adjuvant, were employed at a concentration of $5 \times 10^9$ colony forming units (CFU)/mL. Each innoculation consisted of 12 mL of this material. The following immunization schedule was employed for each cow. Initially a subcutaneous (SQ) innoculation 14 days prior to drying off (D-14) was given. This was followed by an intramammary booster given seven days post drying off (D+7) and a second SQ booster given at D+30. This and similar immunization schedules are taught by the prior art and while the above schedule fully describes the method used, this description is not meant to limit the method of immunization under which the antibodies (immunoglobulins) to *Helicobacter pylori* can be raised since those skilled in the art will recognize and understand that other immunization methods would give similar results.

Upon the birth of the calf of the immunized cow, colostrum was collected, rennet whey prepared and the whey stored frozen at −20° C. until use. The isolation scheme for obtaining the whey is largely as described in U.S. Pat. No. 4,051,235 which is herein incorporated by reference. The basic steps involved are:

Collection and freezing of the bovine colostrum. Thereafter fat is removed from the colostrum. This is achieved by partially thawing the frozen colostrum and removing the upper liquid portion. The remaining material is then completely thawed and centrifugally separated to remove as much of the remaining fat as possible.

The defatted colostrum was precipitated by adding 7.5 mg of calcium chloride per liter of colostrum and by adding 1.5 gram of commercially available rennin per liter of colostrum. The mixture was then thoroughly stirred at 20° C. Thereafter, the solution was permitted to stand for 2-5 hours while the casein in the solution precipitated. The precipitated casein was then removed by filtration. The resulting solution is hereinafter referred to as "bovine colostrum whey" (BCW). The solution was then clarified by filtration and the protein and immunoglobulin concentration were then determined using methods described is below.

EXAMPLE 2

Characterization of Antibody Test Material

The bovine colostrum whey (BCW) samples were analyzed for total protein, immunoglobulin isotype type characterization, IgGl content and for specific anti-*Helicobacter pylori* antibodies. The techniques used for these assays are standard procedures employed in the art and were, respectively, dye binding methods (BioRad), radial immunodiffusion, (ICN Biochemicals), and the enzyme linked immunoassay (ELISA).

The ELISA plates were coated with a *Helicobacter pylori* cell lysate at 3.2 ug/mL. The detecting antibody employed was a conjugate of alkaline phosphatase-coupled to a monoclonal antibody having immunospecificity for bovine IgGl type antibodies. The indicator substrate for the assay was p-nitrophenylphosphate. The extent of color development was measured on a Dynatech ELISA plate reader at a visible wavelength of 490 nm and the data analyzed according to standard statistical methods. The results for these studies are summarized in Table 1. The data illustrates clearly that oral exposure to *Helicobacter pylori* results in over a one hundred fold increase in immunoglobulin (IgGl) concentration in colostral whey as compared to whey obtained from non-immunized cows.

the dominant immunoglobulin isotype contained in BCW (Table 3).

The bacterial agglutination test is a classical procedure used to determine the presence and relative concentration of specific antibody in sera to specific bacteria (e.g. Widal test for typhoid fever). Agglutination involves the aggregation of bacteria into large clumps as a result of the binding of specific antibody to particular sites on the outer surface antigens of the bacterium. Thus, bacterial clumping (agglutination) can be readily observed following the mixing of a suitable bacterial suspension and an immunoglobulin preparation from an animal previously immunized with that bacterium. Estimation of the strength (titer) of a given antibody preparation is accomplished by diluting the antibody (e.g. 2-fold serial dilutions) and determining the last dilution which shows an agglutination effect. Visualization of bacterial agglutination is made by examining the pattern of sedimented bacteria on the bottom of a U-shaped plastic microteter plate. Non-agglutinated bacteria sediment into a tight button whereas agglutinated bacteria are hindered from forming a button and sediment into a diffuse pattern on the bottom of the plastic well.

Test antibody dilutions were made in microtiter plates followed by the addition of appropriately diluted bacteria (formalin fixed *Helicobacter pylori* or *E. coli*). Buffer containing methylene blue was then added to facilitate easy reading of agglutination end points. The plates were examined after an eighteen (18) hour incubation at 4° C. Thereafter, the extent of agglutination was determined and the results expressed as the lowest serial dilution of antibody which exhibited agglutination as defined above.

TABLE 1

CHARACTERIZATION OF BOVINE COLOSTRAL WHEY PREPARATION

| COLOSTRAL WHEY PREPARATION[a] | TOTAL PROTEIN (mg/mL) | mg IgGl/ mL | ELISA[b] TITER/mg IgGl[b] | FOLD DIFFERENCE FROM NON-IMMUNE |
|---|---|---|---|---|
| IMMUNE | 176.2 | 125.2 | 615 | 123 |
| CONTROL (Non-Immunized) | Not Determined | 171.2 | 5 | 1 |

[a]Colostral whey obtained from *Helicobacter pylori* immunized cow and from the non-*Helicobacter pylori* immunized cow (CONTROL).
[b]Nonadjusted ELISA titers on undiluted colostral whey [IMMUNE = 77,000 and CONTROL = 860]. This assay detects antibodies specifically against *Helicobacter pylori*.

EXAMPLE 3

Characterization of *Helicobacter pylori* Antibodies

Specific *Helicobacter pylori* antibodies may be characterized in a number of ways. For the purpose of the present study the biological activity of the immunoglobulins was determined by means of an agglutination assay (Table 2) and the biophysical characterization is provided by a consideration of the physical properties of The results of this study are shown in Table 2. The data indicate clearly that antibodies raised against *Helicobacter pylori* and contained within BCW react specifically at high titers (i.e. dilutions) to *Helicobacter pylori* and do not react significantly with other viral and bacterial antigens. Likewise, similar immunoglobulin preparations from non-immunized cows or cows immunized with unrelated bacterial or viral antigens do not react significantly with *Helicobacter pylori*.

TABLE 2

CHARACTERIZATION OF *HELICOBACTER PYLORI* (*H. pylori*) IMMUNE AND NON-IMMUNE BOVINE LACTOIMMUNOGLOBULIN PREPARATION BY BACTERIAL AGGLUTINATION[a]

| ANTIBODY TEST SAMPLE | | | AGGLUTINATING ANTIBODY | | |
|---|---|---|---|---|---|
| COLOSTRUM REFERENCE | IMMUNIZING ANTIGEN | IgGl (mg/mL) | TEST ANTIGEN | TITER/mL | SPECIFIC ACTIVITY (TITER/mgIgGl) |
| 1 | H. pylori | 75.4 | H. pylori | 256,000 | 3,400 |
| 2 | HRV[b] | 52.4 | H. pylori | 2,560 | 49 |
| 3 | E. coli | 10 | H. pylori | 320 | 32 |
| 4 | None | 27.3 | H. pylori | 1,280 | 47 |
| 1 | H. pylori | 75.4 | E. coli | 640 | 8.5 |
| 2 | HRV | 52.4 | E. coli | 640 | 12 |
| 3 | E. coli | 10 | E. coli | 8,000 | 800 |

TABLE 2-continued

CHARACTERIZATION OF HELICOBACTER PYLORI (H. pylori) IMMUNE AND NON-
IMMUNE BOVINE LACTOIMMUNOGLOBULIN PREPARATION BY
BACTERIAL AGGLUTINATION[a]

| ANTIBODY TEST SAMPLE | | | AGGLUTINATING ANTIBODY | | |
|---|---|---|---|---|---|
| COLOSTRUM REFERENCE | IMMUNIZING ANTIGEN | IgG1 (mg/mL) | TEST ANTIGEN | TITER/mL | SPECIFIC ACTIVITY (TITER/mgIgG1) |
| 4 | None | 27.3 | E. coli | 160 | 5.9 |

[a] H. pylori and E. coli bacteria were adjusted to 8 × 10⁹ cells/mL and added to two-fold antibody dilutions in microtiter plates. Methylene blue (0.01%) was added to the bacterial diluent (0.01 M phosphate - buffered saline pH 7.0) to enhance visualization of agglutinated bacteria.
[b] Human rotavirus (HRV).

The dominant antibody class found in colostrum is immunoglobulin type G (IgG) of the IgG1 isotype subclass. These antibodies possess the physical properties described in Table 3.

TABLE 3

BIOPHYSICAL CHARACTERIZATION OF ANTIBODIES CONTAINED IN COLOSTRUM

| Dominant Immunoglobulin Class: | IgG1 |
|---|---|
| Molecular Weight: | 160,000 Daltons |
| Sedimentation Coefficient ($S_{20,w}$): | 6.7 s |
| Extinction Coefficient ($E_{280}^{1\%}$): | 12.2 |
| Isoelectric Point: | 5.5–6.8 |
| Carbohydrate Content: | 3% |

EXAMPLE 4

Preparation of Feed Material

Following assay, as described above, the BCW samples were added to commercially available Similac ® infant formula (Ross Laboratories) to yield a standard concentration of 17 mg IgG1/mL. Following combination the samples were heat treated and an antibiotic mixture added to result in the production of a material free of viable bacteria. This is a requirement for the gnotobiotic piglet model. The individual concentrations of the antibiotics were selected so as to be noninhibitory for Helicobacter pylori growth only. All other bacteria growth was inhibited.

The control feed was Similac ® containing the same type and amount of antibiotic mixture.

EXAMPLE 5

Experimental Animals

A piglet litter of 73 animals was aseptically delivered and maintained in germ free incubators according to standard procedures for establishing germ free animals.

From this litter 11 animals were randomly divided into two experimental groups:

Group I: 5 Piglets fed control Similac ® nutrient only; and

Group II: 6 Piglets fed Similac ® containing Helicobacter pylori antibody.

Both experimental groups were orally infected with Helicobacter pylori at 3 days of age with $2 \times 10^9$ CFU/mL following pretreatment with Cimetidine.

Proof of Helicobacter pylori infection was established by means of ELISA assays to detect Helicobacter pylori-specific porcine antibodies in serum samples from each piglet as illustrated in Table 4. The data contained in this Table indicates that both groups of animals clearly develop significant antibody levels of all three immunoglobulin isotypes in their sera following infection as compared to preinfection sera.

TABLE 4

ISOTYPE SPECIFIC ELISA TESTING OF INFECTED AND CONTROL GERMFREE PIGLET SERA FOR ANTIBODY TO H. pylori

| PIGLET GROUP AND TIME SAMPLED | MEAN OPTICAL DENSITY ISOTYPE SPECIFIC SERUM ANTIBODY | | |
|---|---|---|---|
| | IgG | IgM | IgA |
| 1. ALL PIGLETS BEFORE INFECTION | <0.01 | <0.02 | <0.03 |
| 2. IMMUNE COLOSTRUM FED AFTER INFECTION | 0.58 | 0.32 | 0.38 |
| 3. CONTROL (SIMILAC) FED AFTER INFECTION | 0.77 | 0.38 | 0.35 |

EXAMPLE 6

Feeding Regimen

Ten days following Helicobacter pylori infection, piglets were fed either Similac ® only (Group I) or Similac ® containing Helicobacter pylori specific antibodies (Group II) at a concentration of 17 mg IgG1/mL. The animals each received 30 mL of feed material three times each day. Following feeding, each animal received 150 mL of milk replacer diet which did not contain antibodies. The feeding protocol continued for a twenty day period.

EXAMPLE 7

Post Protocol Assessment

At age 33 days, blood samples were drawn from each animal and the animals were euthanized and necropsied. The blood samples were processed to serum and analyzed for the presence of porcine anti-Helicobacter pylori antibodies. Gastric epithelium samples (1–2 cm²) from five different anatomic regions were taken at necropsy and subsequently evaluated for bacterial colonization and histologic evidence of infection. The biopsies were taken from the cardiac, fundic, pyloric, antrum and diverticulum regions of the stomach.

Biopsy samples were placed on selective agar plates containing the selected antibiotic mixture and streaked. The innoculated plates were incubated in gas jars in a reduced oxygen atmosphere consisting of 5% $O_2$, 10% $CO_2$ and 80% $N_2$ at 37° C. which is a gas mixture which selectively facilitates *Helicobacter pylori* growth. The plates were examined for bacterial growth after 5-8 days. Suspected *Helicobacter pylori* colonies were subcultured onto fresh medium. Gram stains were performed on both the bacterial growth as well as on the mucoid material associated with the biopsies. Identity of the bacteria was confirmed using standard enzymatic (catalase, oxidase, urease) and antibiotic sensitivity (Nalidixic acid and Cephalothin) assays. The profiles

*Helicobacter pylori* bacteria were isolated from 100% of the control piglets (i.e. those animals receiving nonimmune nutrient) whereas viable *Helicobacter pylori* bacteria were isolated from only 50% of the piglets fed the immune product. Identity of the bacteria as being *Helicobacter pylori* was confirmed using biochemical assays. The differences are significant at the 95% confidence level using the one-sided Students "t" test or the nonparametric ranking approach (Wilcoxin test).

TABLE 5

REISOLATION OF *HELICOBACTER pylori* FROM GERMFREE PIGLETS[a]

| PIGLET NUMBER | FEEDING GROUP[b] | H. pylori COLONY GROWTH[c] | | | | | PIGLETS WITH H. pylori POSITIVE BIOPSIES/TOTAL[d] |
|---|---|---|---|---|---|---|---|
| | | CARDIA | FUNDUS | PYLORUS | ANTRUM | DIVERTICULUM | |
| 1 | I | + | − | + | + | − | 3/5 |
| 2 | I | + | + | + | + | + | 5/5 |
| 3 | I | − | − | − | − | − | 0/5 |
| 4 | I | − | − | − | − | − | 0/5 |
| 5 | I | − | − | − | − | − | 0/5 |
| 6 | I | + | + | − | + | − | 3/5 |
| | | | | | | | 11/30 = 37% |
| 7 | NI | + | + | + | + | + | 5/5 |
| 8 | NI | + | + | + | + | + | 5/5 |
| 9 | NI | + | + | + | + | + | 5/5 |
| 10 | NI | + | − | − | − | + | 2/5 |
| 11 | NI | + | − | + | + | + | 4/5 |
| | | | | | | | 21/25 = 84% |

[a] Each piglet challenged with *H. pylori* (10 days earlier) was fed either *H. pylori* immune colostrum (1.5 g IgG1/90 mL/day in 3 feedings) diluted in Similac alone (non-immune group) for 20 days.
[b] I = Piglets fed diluted immune colostrum. NI = Piglets fed non-immune preparation (Similac RTF).
[c] Based upon colony growth from selective agar plates. *H. pylori* confirmed by appropriate biochemical testing (Urease, Catalase, Oxidase and sensitivity to nalidixic acid and cephalothin).
[d] Statistical evaluation (2 sample, 1-sided T test). Immune fed group significantly less than non-immune group (p = 0.0298).

provided by these assays allow for the accurate definition of the type of bacteria being examined. This methodology is standard in the art. The results for these studies are summarized in Tables 5 and 6.

Data on the reisolation of viable bacteria from the various piglet stomach regions examined is shown in Table 5. A comparison was made between piglets fed the immune Product as compared to those receiving nonimmune nutrient only.

In piglets fed non-immune nutrient, small bacterial colonies typical of *Helicobacter pylori* developed on the agar plates in 84% of the 5 stomach epithelium biopsy sites assayed. In comparison, piglets fed nutrient containing specific anti-*Helicobacter pylori* antibodies, colonies were observed in only 37% of the biopsies. Viable In addition to the above, Gram-stains were performed on the mucoid material isolated with the tissue biopsies following five days of incubation. (*Helicobacter pylori* is a Gram-negative bacterium). Specifically, a determination of the number of biopsy specimens which were positive for Gram-negative bacteria was made. This information is summarized in Table 6. These data confirm the information contained in Table 5 in that the incidence of Gram-negative bacteria found in piglets fed the non-immune nutrient is 78% as compared to the 35% incidence found in piglets fed nutrient containing specific anti-*Helicobacter pylori* antibodies. This difference is significant at the 90% confidence level.

TABLE 6

COMPARISON OF *H. pylori* CULTURE REISOLATION AND GRAM STAIN OF MUCUS

| PIGLETS | FEEDING GROUP[a] | PIGLETS WITH H. pylori POSITIVE BIOPSIES[b]/TOTAL | GRAM STAIN (MUCUS)[c] GNR POSITIVE/ TOTAL TESTED |
|---|---|---|---|
| 1 | I | 3/5 | 5/5 |
| 2 | I | 5/5 | 1/1 |
| 3 | I | 0/5 | 0/5 |
| 4 | I | 0/5 | 1/5 |
| 5 | I | 0/5 | 1/5 |
| 6 | I | 3/5 | 0/2 |
| | | 11/30 = 37% | 8/23 = 35% |
| 7 | NI | 5/5 | 4/5 |
| 8 | NI | 5/5 | 3/4 |
| 9 | NI | 5/5 | 4/5 |
| 10 | NI | 2/5 | 3/4 |
| 11 | NI | 4/5 | 4/5 |
| | | 21/25 = 84% | 18/23 = 78% |

[a] I = Piglets fed diluted immune colostrum. NI = Piglets fed non-immune preparation (Similac RTF).
[b] Based upon colony growth from selective agar plates. *H. pylori* confirmed by appropriate biochemical testing (Urease, Catalase, Oxidase and sensitivity to nalidixic acid and cephalothin).
[c] Gram stain of inoculum mucus from plates with or without typcial *H. pyroli* microcolonies (GNR = Gram Negative Rods).

Of critical importance to the interpretation of the data discussed above is the determination that all experimental animals had indeed been infected with with *Helicobacter pylori* bacteria. Proof of this is indicated by the data contained in Table 4 which illustrates that following infection with *Helicobacter pylori* all of the piglets developed antibodies to *Helicobacter pylori* (i.e. seroconvert) and contain antibodies (immunoglobulins) within their sera exhibiting activity specifically against *Helicobacter pylori*. This was determined by an ELISA analysis of the sera of the piglets upon termination of the experiment. The data contained in Table 4 indicates clearly that all animals developed significant amounts of specific anti-*Helicobacter pylori* antibodies and therefore must have been infected with the *Helicobacter pylori* microorganism.

INDUSTRIAL APPLICABILITY

The presence of *Helicobacter pylori* in the gastrointestinal tract of humans is believed to cause gastritis, previous therapies have serious side effects and often fail to prevent reoccurance of the malady. The medical community has long sought a therapy or preventative to this disorder and the present invention fills that need.

The foregoing detailed description is given for clearness of understanding only, and no unnecessary limitation should be understood therefrom, as modifications will be obvious to those skilled in the art.

We claim:

1. A method of treating a human inflicted with gastritis induced by *Helicobacter pylori*, said *Helicobacter pylori* being capable of colonizing and producing gastritis in humans or gnotobiotic piglets, said method comprising enterally administering to the individual in need of treatment an effective amount of a composition comprising non-denatured immunoglobulins which specifically bind to the bacterium *Helicobacter pylori* in the stomach of a human.

2. A method of treating a person inflicted with *Helicobacter pylori* induced gastritis according to claim 1 wherein said immunoglobulins are isolated from the mammary secretions of cows.

* * * * *

UNITED STATES PATENT AND TRADEMARK OFFICE
CERTIFICATE OF CORRECTION

PATENT NO.   : 5,260,057
DATED        : November 9, 1993
INVENTOR(S)  : C.Cordle, J. Schaller It is certified that error appears in the above-identified patent and that said Letters Patent is hereby corrected as shown below:

Column 3, line 6, "Rauns" should be --Rauws--.

Column 9, line 60, "73" should be --13--.

Signed and Sealed this

Seventeenth Day of May, 1994

Attest:

BRUCE LEHMAN

Attesting Officer    Commissioner of Patents and Trademarks